(12) United States Patent
Weyler et al.

(10) Patent No.: US 8,809,431 B2
(45) Date of Patent: Aug. 19, 2014

(54) PROCESS FOR STABILIZING OLEFINICALLY UNSATURATED MONOMERS

(75) Inventors: Stefanie Weyler, Huenxe (DE); Phillip James, Tenby (GB); Oliver Erpeldinger, Wuelfrath (DE); Manfred Neumann, Marl (DE); Frank Kraushaar, Essen (DE)

(73) Assignee: Evonik Degussa GmbH, Essen (DE)

( * ) Notice: Subject to any disclaimer, the term of this patent is extended or adjusted under 35 U.S.C. 154(b) by 7 days.

(21) Appl. No.: 13/342,661

(22) Filed: Jan. 3, 2012

(65) Prior Publication Data

US 2012/0101295 A1 Apr. 26, 2012

Related U.S. Application Data

(62) Division of application No. 12/262,875, filed on Oct. 31, 2008, now Pat. No. 8,128,804.

(30) Foreign Application Priority Data

Nov. 2, 2007 (DE) .......................... 10 2007 052 891

(51) Int. Cl.
*C08K 5/04* (2006.01)
*C08K 5/07* (2006.01)

(52) U.S. Cl.
USPC ...................................... 524/320; 208/48 AA

(58) Field of Classification Search
None
See application file for complete search history.

(56) References Cited

U.S. PATENT DOCUMENTS

| | | | |
|---|---|---|---|
| 3,061,586 A | 10/1962 | Thompson | |
| 3,530,193 A | 9/1970 | Starnes, Jr. | |
| 4,003,800 A | 1/1977 | Bacha et al. | |
| 4,040,911 A | 8/1977 | Bacha et al. | |
| 4,654,451 A | 3/1987 | Miller et al. | |
| 7,030,279 B1 | 4/2006 | Tanielyan et al. | |
| 7,045,647 B2 | 5/2006 | Benage | |
| 7,046,647 B2 | 5/2006 | Oba et al. | |
| 8,212,081 B2 | 7/2012 | Rinker et al. | |
| 2004/0034247 A1 | 2/2004 | Eldin | |
| 2005/0027150 A1 | 2/2005 | Eldin et al. | |
| 2005/0256312 A1 | 11/2005 | Osterholt et al. | |
| 2006/0020089 A1 | 1/2006 | Merrill | |
| 2006/0283699 A1 | 12/2006 | Ma et al. | |
| 2007/0208204 A1 | 9/2007 | Meyer et al. | |

FOREIGN PATENT DOCUMENTS

| | | |
|---|---|---|
| DE | 694 19 662 T2 | 1/2000 |
| DE | 696 09 110 T2 | 3/2001 |
| EP | 0 626 377 A1 | 11/1994 |
| EP | 0 737 659 B1 | 7/2000 |
| EP | 0 737 660 B1 | 8/2002 |
| JP | 9-176215 A | 7/1997 |
| JP | 2003-515656 A | 5/2003 |

(Continued)

OTHER PUBLICATIONS

C.M. Orlando, "Quinone Methide Chemistry. The Benzylic Oxidative Methoxylation of 2, 6-Di-tert-butyl-p-cresol", J. Org. Chem., vol. 35, No. 11, XP-002514061, 1970, pp. 3714-3717.
Von Eugen Muller, et al., "Instabile Aroxyle", Justus Liebigs Annalen Der Chemie, Verlag Chemie GMBH, Weinheim, De, vol. 645, XP-009096429, Jan. 1, 1961, pp. 66-78.

(Continued)

*Primary Examiner* — Tam M Nguyen
(74) *Attorney, Agent, or Firm* — Oblon, Spivak, McClelland, Maier & Neustadt, L.L.P.

(57) ABSTRACT

An olefinically unsaturated monomer is stabilized by a retarder-containing composition which comprises a solvent and a quinone methide as a retarder.

11 Claims, 1 Drawing Sheet

(56) References Cited

FOREIGN PATENT DOCUMENTS

| | | |
|---|---|---|
| JP | 2004-511569 A | 4/2004 |
| JP | 2004-513985 A | 5/2004 |
| WO | WO 99/48896 | 9/1999 |
| WO | WO 01/40404 A1 | 6/2001 |
| WO | WO 02/33025 A2 | 4/2002 |
| WO | WO 02/33026 A1 | 4/2002 |

OTHER PUBLICATIONS

A. A. Yassin, et al., "The Mechanisms of Retardation and Inhibition in Radical Polymerizatins by Quinones", European Polymer Journal, vol. 9, No. 7, XP-023321771, Jul. 1, 1973, pp. 657-667.
European Search Report mailed Feb. 9, 2009.
Taiwanese Office Action issued Jun. 20, 2013 in Patent Application No. 097141190 (English Translation only).
Japanese Office Action issued Jun. 24, 2013 in Patent Application No. 2008-282889 (German Translation only).

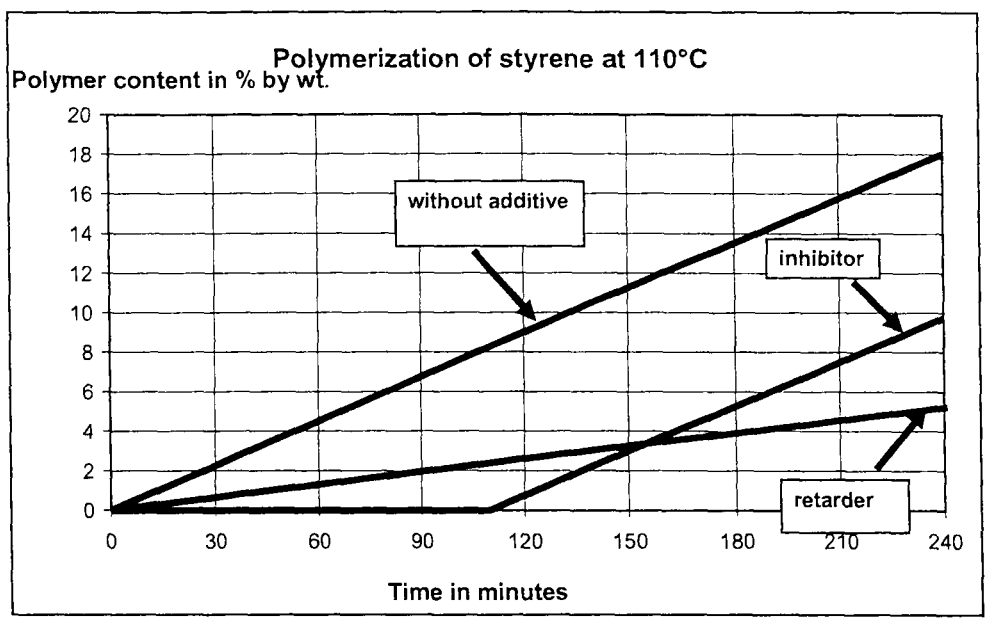

PROCESS FOR STABILIZING OLEFINICALLY UNSATURATED MONOMERS

BACKGROUND OF THE INVENTION

1. Field of the Invention

The invention relates to a stabilizer composition which is suitable for stabilizing an olefinically unsaturated monomer during production, purification and storage, and to a corresponding process for stabilizing an olefinically unsaturated monomer.

2. Discussion of the Background

During the preparation of olefinically unsaturated monomers, for example ethene, butadiene, isoprene, vinyl acetate, (meth)acrylic acid, (meth)acrylates, acrolein, acrylonitrile or vinyl-substituted aromatics, these olefinically unsaturated monomers are subjected to several purification process steps, for example distillation or extraction, in order to remove undesired by-products or impurities. The production and distillation process steps in particular are performed at elevated temperatures.

Olefinically unsaturated monomers therefore have a tendency to unwanted polymerization as early as during the preparation and/or purification process. The risk of polymerization exists in all abovementioned monomers—particularly at elevated temperature. Some of these olefinically unsaturated monomers, for example butadiene, however, even during storage or in the course of transport, also have a tendency to a spontaneous, usually strongly exothermic and therefore hazardous polymerization.

However, the comparatively creeping polymerization of olefinically unsaturated monomers during production and purification is also undesired. Firstly, it results in deposits of the polymers in the reactors and columns, and secondly in a reduction in the amount of available monomers. Deposits of the polymer can lead, among other results, to reduced heat transfer in individual plant parts, and hence to a reduced productivity.

In addition, plant components, for example filters, can become covered and be blocked with the undesired polymer. This has the consequence of unplanned interruptions of production, in order to be able to carry out cleaning of the plant. Every shutdown firstly causes repair and cleaning costs; secondly, a shutdown also causes a production shortfall, and so it is always attempted to avoid them or to minimize their number as far as possible.

Consequently, additives, which are referred to either as polymerization inhibitors or as retarders, are added to the olefinically unsaturated monomers generally as early as during the preparation process. Polymerization inhibitors are, as the name actually states, capable of completely preventing undesired polymerization. Polymerization inhibitors are, however, consumed rapidly, and so the polymer content rises just as significantly within a short time as if no additive had been added. Polymerization retarders, in contrast, can never completely prevent polymerization, but rather only slow it. At the same time, they are consumed significantly more slowly than polymerization inhibitors.

The presence of both types of polymerization inhibition in monomer production is justified. Constant supply of fresh polymerization inhibitors can achieve the effect that the polymerization content is kept at a very low level or polymerization can be prevented completely during a production process proceeding without disruption. Polymerization retarders are, in contrast, of great importance in the case of stoppage of the additive supply, since, as a result of their longer activity, they still prevent significant polymerization even when the polymerization inhibitors have long since been consumed. In general, both types of additives are used in combination with one another.

Polymerization inhibitors, which are frequently described in the literature are, for example, so-called stable free nitroxyl radicals such as 2,2,6,6-tetramethylpiperidine N-oxyl (TEMPO) or derivatives thereof. The polymerization retarders used are generally nitroaromatics, for example 2,4-dinitro-6-sec-butylphenol (DNBP), 2,4-dinitrophenol (DNP) or 4,6-dinitro-ortho-cresol (DNOC). Nitroaromatics exhibit good retarder properties, but also possess serious disadvantages. For instance, they are generally highly toxic and possess carcinogenic, mutagenic and/or reproduction-toxic properties. The use of these nitroaromatics therefore entails correspondingly high safety precautions on the part of the user. Furthermore, in the event of incineration of the nitroaromatic-containing residues of the distillation columns, environmentally harmful NO gases are released. Attempts are also made to avoid this as far as possible.

To prevent polymerization in the preparation of vinylically unsaturated compounds, as well as the abovementioned substance classes, there are also many further additives which are known from the literature and can be used, for example C- and/or N-nitroso compounds, hydroxylamines and oximes. All of these substance classes, just like the nitroaromatics, have quite a high proportion of undesired nitrogen atoms which can leave as $NO_x$ in the later incineration process of the distillation residues.

A further known substance class for preventing this undesired polymerization is that of quinone methides of the formula I:

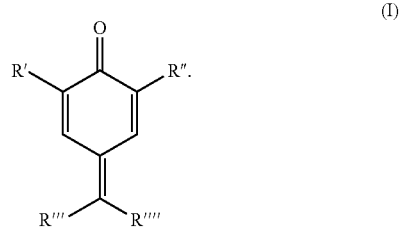

The use of this substance class for inhibiting the polymerization of styrene is described by Bacha et al. in U.S. Pat. No. 4,003,800 and also in U.S. Pat. No. 4,040,911, where the substituents of the R''' and R'''' type may be hydrogen, an alkyl group, a cycloalkyl group or an optionally alkyl-substituted phenyl group.

EP 0 737 659 and EP 0 737 660 also describe quinone methides for stabilization of monomers, the quinone methides used in EP 0 737 659 having hydrogen as the substituent of the R''' type, and aryl or heteroaryl groups which may optionally have further substituents as the substituent of the R'''' type. EP 0 737 660, in contrast, describes the use of quinone methides with substituents of the R'''' type selected from —CN, —COOR, —COR, —OCOR, —CONRR and —PO(OR)$_2$, where R may be hydrogen or an alkyl, cycloalkyl, phenyl or aryl group. In EP 0 737 660 too, the use of these quinone methides with strongly electron-withdrawing substituents in combination with nitroxyl radicals is described.

The use of quinone methides in combination with other known additives for inhibiting polymerization is described by some patent publications. Quinone methides in which R'''=hydrogen and R''''=aryl groups which may optionally also be substituted are described in WO 99/48896 and US 2005/0027150 in combination with hydroxylamines. In contrast, US 2006/0020089 describes these quinone methides in combination with 4-tert-butylcatechol. Quinone methides where R'''=hydrogen and R''''=hydrogen or an alkyl or aryl group in combination with hydroxylamines and catechol derivatives are described by Eldin in US 2004/0034247. Nakajima et al. describe, in addition, sulphonic acids and quinone methides where R'''=hydrogen and R''''=phenyl group which may optionally be substituted for inhibiting polymerization, and it is also additionally possible to use stable free nitroxyl radicals.

A composition of additives for inhibiting polymerization is described by WO 01/40404 A1. This describes a composition consisting of a hydrogen donor or an electron acceptor and a nitroxyl radical, for which conceivable electron acceptors include quinone methides.

Ma et al. describe, in US 2006/0283699, a polymerization inhibitor composition which comprises at least one nitroso compound as a polymerization inhibitor. This polymerization inhibitor composition may comprise, among other substances, nitroxyl radicals and quinone methides.

A polymerization inhibitor composition consisting of at least one C-nitrosoaniline and a quinone imine oxide and at least one compound, selected from compounds including quinone alkides, nitroxyl compounds, is described by Benage et al. in WO 02/33025 A2.

SUMMARY OF THE INVENTION

It was an object of the present invention to provide a stabilizer composition for olefinically unsaturated monomers with a reduced toxicity compared to the background art. More particularly, it was an object to provide a retarder which has a reduced toxicity compared to the currently frequently used nitroaromatics, but at the same time has at least a comparable retarder activity compared to retarders according to the background art and which can have synergistic effects with the nitroxyl radicals.

This and other objects have been achieved by the present invention the first embodiment of which includes a process for stabilizing olefinically unsaturated monomers, comprising:
adding a retarder-containing composition to
(i) an olefinically unsaturated monomer, or
(ii) a monomer mixture which comprises at least one olefinically unsaturated monomer;
wherein said retarder-containing composition (AB) comprises
(A) a solvent which is a saturated or unsaturated, branched and/or unbranched, ring-closed and/or open-chain aliphatic or aromatic hydrocarbon, ether or ester, each of which has 4 to 20 carbon atoms, or methanol, and
(B) at least one retarder of the formula (II)

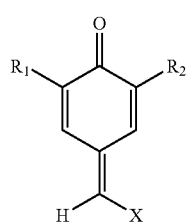

(II)

wherein
X=halogen, —O—$R_3$ or —S—$R_3$,
$R_1$, $R_2$ and $R_3$=hydrogen, alkyl having 1 to 15 carbon atoms, cycloalkyl having 3 to 15 carbon atoms or aryl group having 6 to 14 carbon atoms,
wherein the substituents $R_1$, $R_2$ and $R_3$ are the same or different and are substituted or unsubstituted.

BRIEF DESCRIPTION OF DRAWING

The FIGURE shows the dependence of the polymer concentration on the time using either no additive, or an inhibitor or retarder.

DETAILED DESCRIPTION OF THE INVENTION

It has been found that, surprisingly, compounds of the formula (II) are suitable as retarders for olefinically unsaturated monomers. For instance, compounds of the formula (II) have comparable retarder activities compared to the conventional retarder 2,4-dinitro-6-sec-butylphenol (DNBP) (see examples 7 and 10). This was completely surprising since the background art does mention the quinone methides in connection with inhibition of polymerization, but these quinone methides, which have strongly electron-withdrawing groups as X substituents, are conventional polymerization inhibitors which have no retarder activities whatsoever (see examples 4-6). In contrast, not all compounds of the substance class of the quinone methides in turn exhibit action with regard to inhibition of polymerization (see example 2).

The quinone methides of the formula (II) are thus, in contrast, retarders with astonishingly high activity, which, in combination with nitroxyl radicals, have improved action as a stabilizer composition compared to the combination of nitroxyl radicals with nitroaromatics, for example DNBP (see examples 13-17). In addition, the combination of the quinone methides of the formula (II) and nitroxyl radicals has a synergistic effect compared to the individual substances.

On the basis of the structure of the quinone methides, a lower toxicity compared to the nitroaromatics is expected. The use of these quinone methides of the formula (II) likewise allows the emission of $NO_x$ offgases to be reduced compared to the $NO_x$ emissions in the case of use of nitroaromatics as retarders.

The quinone methides of the formula (II) are stable in all nonpolar solvents, and so use of these quinone methides as a solution enables simple handling. It is advantageous that the solvents need not necessarily be the monomer to be stabilized. The retarder action is not impaired even when the quinone methide is added in other solvents (see examples 10a-10c).

The invention provides a process for stabilizing olefinically unsaturated monomers, wherein a retarder-containing composition (AB) which comprises
a solvent (A) selected from saturated or unsaturated, branched and/or unbranched, ring-closed and/or open-chain aliphatic or aromatic hydrocarbons, ethers or esters, each of which has 4 to 20 carbon atoms, or methanol, and
at least one retarder (B) of the formula (II)

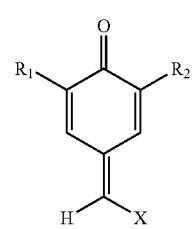

(II)

where:
X=halogen, —O—$R_3$ or —S—$R_3$,
$R_1$, $R_2$ and $R_3$=hydrogen, alkyl having 1 to 15 carbon atoms, cycloalkyl having 3 to 15 carbon atoms or aryl group having 6 to 14 carbon atoms, where the substituents of the $R_1$, $R_2$ and $R_3$ type are the same or different and are substituted or unsubstituted, is added to an olefinically unsaturated monomer or to a monomer mixture which comprises at least one olefinically unsaturated monomer.

The invention further provides a monomer composition which comprises from 10 ppb (m/m) to 100 000 ppm (m/m) including all subvalues in between, based on the olefinically unsaturated monomer, of at least one retarder (B) of the formula (II).

This invention likewise provides a retarder-containing composition which comprises a solvent (A) selected from saturated or unsaturated, branched and/or unbranched, ring-closed and/or open-chain aliphatic or aromatic hydrocarbons, ethers or esters, each of which has 4 to 20 carbon atoms, or methanol, and at least one retarder (B) of the formula (II).

In the process according to the invention for stabilizing olefinically unsaturated monomers, a retarder-containing composition (AB) which comprises a solvent (A) selected from saturated or unsaturated, branched and/or unbranched, ring-closed and/or open-chain aliphatic or aromatic hydrocarbons, ethers or esters, each of which has 4 to 20 carbon atoms, or methanol, and at least one retarder (B) of the formula (II)

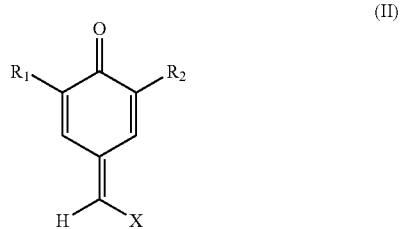

where:

X=halogen, —O—$R_3$ or —S—$R_3$, $R_1$, $R_2$ and $R_3$=hydrogen, alkyl having 1 to 15 carbon atoms, cycloalkyl having 3 to 15 carbon atoms or aryl group having 6 to 14 carbon atoms, where the substituents of the $R_1$, $R_2$ and $R_3$ type are the same or different and are substituted or unsubstituted, is added to an olefinically unsaturated monomer or to a monomer mixture which comprises at least one olefinically unsaturated monomer.

Particular preference is given in the process according to the invention to using a retarder-containing composition (AB) which comprises from 45.0 to 99.9% by weight of the solvent (A) and
from 0.1 to 55.0% by weight of the retarder (B), but particular preference is given to using a retarder-containing composition (AB) which comprises from 60.0 to 98.0% by weight of the solvent (A) and
from 2.0 to 40.0% by weight of the retarder (B). All amounts given include all subvalues in between the lower and upper limit.

In the process according to the invention, it is advantageous to ensure a suitable solvent which is compatible firstly with the olefinically unsaturated monomer, but also with the retarder (B), and that there cannot be any undesired reactions.

Suitable solvents (A) in the process according to the invention are therefore nonpolar aromatic or aliphatic solvents. Advantageous solvents (A) for this purpose are those selected from benzene, mono- or polyalkylated aromatics, alkanes, cycloalkanes, ethers or esters having in each case a number of carbon atoms of 6 to 15. In the process according to the invention, particular preference is given to using benzene, toluene, ethylbenzene, xylene or styrene. In a further embodiment of the process according to the invention, it is also possible to use methanol. In the process according to the invention, the solvents (A) used may thus be benzene, toluene, ethylbenzene, xylene, styrene or methanol. In the process according to the invention, it is also possible to use mixtures of suitable solvents (A).

In the context of this invention, a retarder (B) is understood to mean a compound which is capable of greatly slowing polymerization of an olefinically unsaturated monomer. The amount of polymer which forms within a given time in the case of an olefinically unsaturated monomer with addition of a retarder is therefore lower than the amount of polymer which is formed within this time in the case of an olefinically unsaturated monomer without addition of a retarder.

The retarders used in the process according to the invention are preferably exclusively retarders of the formula (II). The use of nitro- or nitrosoaromatics as retarders is avoided here. More particularly, retarders (B) of the formula (II) which have, as the substituent of the X type, an O—$R_3$ group are used. In addition, in the process according to the invention, more particularly, retarders (B) of the formula (II) which have, as substituents of the $R_1$ and/or $R_2$ type, a methyl group or tert-butyl group are used. Suitable substituents of the $R_3$ type in the process according to the invention are alkyl or aryl groups, the alkyl groups preferably having 1 to 6 carbon atoms. In the process according to the invention, particular preference is given to using retarders (B) which have, as substituents of the $R_3$ type, an alkyl group having 1 to 6 carbon atoms, more particularly a methyl or ethyl group.

In the process according to the invention, very particular preference is given to using a retarder (B) of the formula (II) which has, as substituents of the $R_1$ type and $R_2$ type, a methyl or tert-butyl group, and, as the substituent of the $R_3$ type, an alkyl group having 1 to 6 carbon atoms, especially a methyl or ethyl group.

In the process according to the invention, it is also possible to use mixtures of these retarders (B).

In the context of this invention, olefinically unsaturated monomers are understood to mean compounds which have at least one C—C double bond and are capable of entering into a polymerization reaction.

In the process according to the invention, preference is given to using at least one olefinically unsaturated monomer selected from vinyl-substituted aromatics, for example divinylbenzene or styrene, alk-1-enes or alka-1,3-dienes, which may be either substituted or unsubstituted, for example ethene, propene or propylene, butadiene, vinyl acetate, (meth)acrylate, acrylonitrile, acrolein, N-vinylformamide, chloroprene, isoprene. Preference is given to using olefinically unsaturated monomers selected from ethene, propene or propylene, butadiene, isoprene, divinylbenzene or styrene. In the process according to the invention, particular preference is given to using butadiene or styrene.

In the process according to the invention, it is possible to use either one compound of olefinically unsaturated monomers or a mixture of different olefinically unsaturated monomers.

In the process according to the invention, the retarder-containing composition (AB) is preferably added as a solution to the olefinically unsaturated monomers.

Advantageously, as well as the retarder-containing composition (AB) in the process according to the invention, a polymerization inhibitor-containing composition (CD) should additionally also be added to the monomer or to the monomer mixture. Preference is given to adding to the monomer or to the monomer mixture a polymerization inhibitor-containing composition (CD) which comprises a solvent (C) selected from saturated or unsaturated, branched and/or unbranched, ring-closed and/or open-chain aliphatic or aromatic hydrocarbons which have 4 to 20 carbon atoms, or alcohols or ethers having in each case 2 to 20 carbon atoms, or alkyl acetates where the alkyl group of this ester likewise has 2 to 20 carbon atoms, or water, and at least one polymerization inhibitor (D) of the formula (IV)

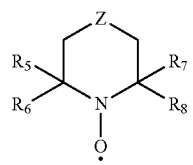

(IV)

where:

$R_5$, $R_6$, $R_7$ and $R_8$=alkyl group having in each case 1 to 4 carbon atoms, Z=>$CR_9R_{10}$, >C=O, >CH—OH, >CH—$NR_9R_{10}$, >CH-Hal, >CH—$OR_9$, >CH—$COOR_9$, >CH—O—CO—$NHR_9$,

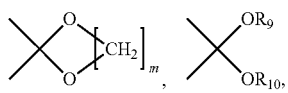

$R_9$, $R_{10}$=hydrogen, alkyl group having in each case 1 to 6 carbon atoms,

Hal=fluorine, chlorine, bromine or iodine, m=1 to 4, where the substituents of the $R_5$, $R_6$, $R_7$, $R_8$, $R_9$ and $R_{10}$ type are the same or different and are substituted or unsubstituted.

In the process according to the invention, particular preference is given to adding to the monomer a polymerization inhibitor-containing composition (CD) which comprises from 35.0 to 99.9% by weight of the solvent (C) and from 0.1 to 65.0% by weight of the polymerization inhibitor (D);

very particular preference is given to adding a composition (CD) which comprises from 40.0 to 95.0% by weight of the solvent (C) and from 5.0 to 60.0% by weight of the polymerization inhibitor (D). All amounts given include all subvalues in between the lower and upper limit.

The solvents (C) used are preferably solvents selected from benzene, mono- or polyalkylated aromatics, alkanes or cycloalkanes having in each case a carbon number of 6 to 15. In a further embodiment of the process according to the invention, it is also possible to use an alcohol selected from methanol, ethanol, n-butanol, or an alkyl acetate selected from ethyl acetate, vinyl acetate and butyl acetate, or water as the solvent (C). The use of a mixture of different solvents (C) in this process is also conceivable.

In the context of this invention, a polymerization inhibitor (D) is understood to mean a compound which is capable of virtually completely preventing polymerization of the olefinically unsaturated monomer for a certain period. The period until polymerization occurs in the case of an olefinically unsaturated monomer without a polymerization inhibitor is therefore shorter than the period in the case of an olefinically unsaturated monomer with a polymerization inhibitor.

In the process according to the invention, preference is given to using, as well as the retarder (B), a polymerization inhibitor (D) of the formula (IV) where $R_5$, $R_6$, $R_7$ and $R_8$=methyl group. In the process according to the invention, very particular preference is given to using 2,2,6,6-tetramethylpiperidine N-oxyl (TEMPO), 4-acetamido-2,2,6,6-tetramethylpiperidine N-oxyl (AA-TEMPO), 4-hydroxy-2,2,6,6-tetramethylpiperidine N-oxyl (4-hydroxy-TEMPO), 4-oxo-2,2,6,6-tetramethylpiperidine N-oxyl (oxo-TEMPO), a compound of the formula (IV) where $R_5$, $R_6$, $R_7$ and $R_8$=methyl group and Z=>CH—$OR_9$ where $R_9$=alkyl group having 1 to 6 carbon atoms and/or a compound of the formula (IV) where $R_5$, $R_6$, $R_7$ and $R_8$=methyl group and

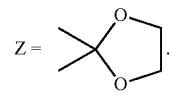

In the process according to the invention, it is also possible to use mixtures of these polymerization inhibitors (D).

In the process according to the invention, it is possible to dissolve the retarder (B) and the polymerization inhibitor (D) independently in different solvents. However, it is advantageous to dissolve both the retarder (B) and the polymerization inhibitors (D) in the same solvent. The two compositions (AB) and (CD) can be added to the monomers separately from one another at different times or at the same time and if appropriate at different metering rates or at the same metering rate. The two compositions (AB) and (CD) can also first be mixed and then supplied to the monomer. Preference is given to adding the two compositions (AB) and (CD) to the monomers separately from one another.

In this context, the compositions (AB) and (CD) can also be added to the olefinically unsaturated monomers during a process, for example preparation or purification process. These compositions can be added to the unsaturated monomers or monomer mixtures by standard background art methods. Advantageously, these compositions can be added in the process according to the invention in any feed stream or outlet of a distillation column, into the inlet and outlet of a heat exchanger or of an evaporator ("boiler") or into the inlet and outlet of a condenser. In addition, in the process according to the invention, these compositions (AB) and if appropriate (CD) can also be added in storage tanks for the olefinically unsaturated monomers.

The term "effective amount" of retarder or polymerization inhibitor in the context of this invention is understood to mean the amount of retarder or polymerization inhibitor which is needed to delay or to prevent the premature polymerization of the olefinically unsaturated monomers. This effective amount depends on the conditions under which the olefinically unsaturated monomer is stored or handled. For example, in the case of distillation of the unsaturated monomer, owing to the relatively high temperatures and the relatively high concentration of impurities, a higher amount of the retarder or polymerization inhibitor is needed than in the case of storage of the monomer.

Preferably, in the process according to the invention, a total of 100 ppb (m/m) to 100 000 ppm (m/m), more preferably of 1 ppm (m/m) to 10 000 ppm (m/m) and most preferably of 10 ppm (m/m) to 2500 ppm (m/m) of retarder (B) and polymerization inhibitor (D), based on the olefinically unsaturated monomer, is added to the olefinically unsaturated monomer or to the monomer mixture. All amounts given include all subvalues in between the lower and upper limit.

The monomer composition of the invention comprises from 10 ppb (m/m) to 100 000 ppm (m/m) (including all subvalues in between the lower and upper limit), based on the olefinically unsaturated monomer, of at least one retarder (B) of the formula (II),

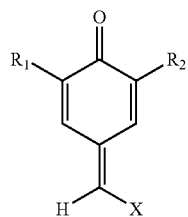

where:
$X$=halogen, —O—$R_3$ or —S—$R_3$,
$R_1$, $R_2$ and $R_3$=hydrogen, alkyl having 1 to 15 carbon atoms, cycloalkyl having 3 to 15 carbon atoms or aryl group having 6 to 14 carbon atoms,
where the substituents of the $R_1$, $R_2$ and $R_3$ type are the same or different and are substituted or unsubstituted.

The monomer composition more preferably comprises 1 ppm (m/m) to 10 000 ppm (m/m), most preferably 10 ppm (m/m) to 2500 ppm (m/m), of the retarder (B). All amounts given include all subvalues in between the lower and upper limit.

The retarders comprised in the monomer composition of the invention are preferably exclusively retarders of the formula (II). Nitro- or nitrosoaromatics as retarders are dispensed with here.

The monomer composition of the invention comprises especially retarders (B) of the formula (II) which have, as the substituent of the X type, an O—$R_3$ group. In addition, the monomer composition of the invention may comprise retarders (B) of the formula (II) which have, as substituents of the $R_1$ and/or $R_2$ type, a methyl group or tert-butyl group. Suitable substituents of the $R_3$ type are the alkyl or aryl groups, the alkyl groups preferably having 1 to 6 carbon atoms. More preferably, the monomer composition comprises a retarder (B) which has, as substituents of the $R_3$ type, alkyl groups having 1 to 6 carbon atoms, especially a methyl or ethyl group.

Most preferably, the monomer compositions of the invention comprise a retarder (B) of the formula (II) which comprises, as substituents of the $R_1$ type and $R_2$ type, a methyl or tert-butyl group, and, as the substituent of the $R_3$ type, an alkyl group having 1 to 6 carbon atoms, especially a methyl or ethyl group.

The monomer composition may also comprise a mixture of these retarders (B).

The monomer composition preferably comprises at least one olefinically unsaturated monomer selected from vinyl-substituted aromatics, for example divinylbenzene or styrene, alk-1-enes or alka-1,3-dienes, which may be either substituted or unsubstituted, for example ethene, propene or propylene, butadiene, vinyl acetate, (meth)acrylate, acrylonitrile, acrolein, N-vinylformamide, chloroprene, isoprene. The monomer composition preferably comprises olefinically unsaturated monomers selected from ethene, propene or propylene, butadiene, isoprene, divinylbenzene or styrene. The monomer composition of the invention more preferably comprises butadiene or styrene.

The monomer composition may comprise either one compound of olefinically unsaturated monomers or a mixture of different olefinically unsaturated monomers.

It is advantageous when the monomer composition, as well as the retarder (B), also comprises a polymerization inhibitor (D) of the formula (IV). This monomer composition preferably comprises a polymerization inhibitor (D) of the formula (IV) where $R_5$, $R_6$, $R_7$ and $R_8$=methyl group. Most preferably, the monomer compositions comprise 2,2,6,6-tetramethylpiperidine N-oxyl (TEMPO), 4-acetamido-2,2,6,6-tetramethylpiperidine N-oxyl (AA-TEMPO), 4-hydroxy-2,2,6,6-tetramethylpiperidine N-oxyl (4-hydroxy-TEMPO), 4-oxo-2,2,6,6-tetramethylpiperidine N-oxyl (oxo-TEMPO), a compound of the formula (IV) where $R_5$, $R_6$, $R_7$ and $R_8$=methyl group and Z=>CH—O$R_9$ where $R_9$=alkyl group having 1 to 6 carbon atoms and/or a compound of the formula (IV) where $R_5$, $R_6$, $R_7$ and $R_8$=methyl group and

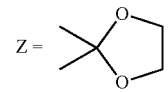

as polymerization inhibitors (D).

For instance, the monomer composition may also comprise mixtures of these polymerization inhibitors (D).

The monomer composition preferably comprises the retarder (B) and the polymerization inhibitor (D) in a total of 10 ppb (m/m) to 100 000 ppm (m/m), more preferably of 1 ppm (m/m) to 10 000 ppm (m/m) and most preferably of 10 ppm (m/m) to 2500 ppm (m/m), based on the olefinically unsaturated monomer. All amounts given include all subvalues in between the lower and upper limit.

The retarder-containing composition comprises
a solvent (A) selected from saturated or unsaturated, branched and/or unbranched, ring-closed and/or open-chain aliphatic or aromatic hydrocarbons, ethers or esters, each of which has 4 to 20 carbon atoms, or methanol, and
at least one retarder (B) of the formula (II)

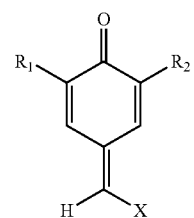

where:
$X$=halogen, —O—$R_3$ or —S—$R_3$,
$R_1$, $R_2$ and $R_3$=hydrogen, alkyl having 1 to 15 carbon atoms, cycloalkyl having 3 to 15 carbon atoms or aryl group having 6 to 14 carbon atoms,
where the substituents of the $R_1$, $R_2$ and $R_3$ type are the same or different and are substituted or unsubstituted.

The retarder-containing composition preferably comprises
from 45.0 to 99.9% by weight of the solvent (A) and
from 0.1 to 55.0% by weight of the retarder (B),
but more preferably comprises
from 60.0 to 98.0% by weight of the solvent (A) and
from 2.0 to 40.0% by weight of the retarder (B). All amounts given include all subvalues in between the lower and upper limit.

In the retarder-containing composition of the invention, it is advantageous to ensure a suitable solvent which is compatible firstly with the olefinically unsaturated monomer for which this retarder-containing composition is to be used for inhibition of polymerization, but also with the retarder (B), and that there can be no undesired reactions.

Suitable solvents (A) for the retarder-containing composition of the invention are therefore nonpolar aromatic or aliphatic solvents. Advantageous solvents for this purpose are selected from benzene, mono- or polyalkylated aromatics, and alkanes, cycloalkanes, ethers or esters having in each case a carbon number of 6 to 15. The retarder-containing composition more preferably comprises benzene, toluene, ethylbenzene, xylene or styrene. In a further embodiment of the retarder-containing composition, it may also comprise methanol as the solvent (A). The retarder-containing composition may thus comprise, as solvents (A), benzene, toluene, ethylbenzene, xylene, styrene or methanol. The retarder-containing composition may also comprise mixtures of suitable solvents (A).

As retarders, the retarder-containing composition preferably comprises exclusively retarders of the formula (II). Nitro- or nitrosoaromatics as retarders are preferably dispensed with here.

The retarder-containing composition may comprise especially retarders (B) of the formula (II) which have, as the substituent of the X type, an O—$R_3$ group. In addition, the retarder-containing composition comprises especially retarders (B) of the formula (II) which have, as substituents of the $R_1$ and/or $R_2$ type, a methyl group or tert-butyl group. Suitable substituents of the $R_3$ type are alkyl or aryl groups, the alkyl groups having preferably 1 to 6 carbon atoms. The retarder-containing composition more preferably comprises retarders (B) which have, as substituents of the $R_3$ type, an alkyl group having 1 to 6 carbon atoms, especially a methyl or ethyl group.

Most preferably, the retarder-containing composition comprises retarders (B) of the formula (II) which have, as substituents of the $R_1$ type and $R_2$ type, a methyl or tert-butyl group, and as the substituent of the $R_3$ type, an alkyl group having 1 to 6 carbon atoms, especially a methyl or ethyl group.

The retarder-containing composition may also comprise a mixture of different retarders (B).

In a preferred embodiment, $R_1$, $R_2$ and $R_3$ in the above formulas may be substituted with at least one group selected from —O-alkyl, —O-aryl, —COO-alkyl, halogen, —$NH_2$, —NHalkyl, —N(alkyl)$_2$. $R_5$, $R_6$, $R_7$ and $R_8$ in the above formulas are preferably unsubstituted. $R_9$ and $R_{10}$ may preferably be substituted with —O-alkyl and/or —O-aryl.

In one embodiment, the retarder (B) is dissolved in a solvent (A), and the polymerization inhibitor (D) is also dissolved, in a solvent (C). These two solvents (A) and (C) may be the same, but do not have to be. Preferably, the two active ingredients (B) and (D) are being delivered separately as solutions and are also being introduced separately into the system. In another preferred embodiment, in order to keep the number of compounds in the system small, one and the same compound is used as the solvent. In this case, solvents (A) and (C) are chemically identical.

In one embodiment, the retarder can have synergistic effects with nitroxyl radicals.

Within the meaning of this application, a synergistic effect is to be understood as follows: the effect with regard to inhibition by joint use of the retarder (B) and of the polymerization inhibitor (D) is greater than expected. Measurements of the effect of the individual compounds are described in both Examples 10 and 12.

If, as in Example 15, 10 ppm of DTBMeOQM and 100 ppm of 4-hydroxy-TEMPO are used, a purely theoretical calculation suggests that a duration—until the polymer content reaches 2 wt %—of approximately 110 minutes (0.1*181+ 1*92) would be expected. In actual fact, a duration of 218 minutes is measured (see Example 15), and so this value is much longer than the expected value. The effect of the combination of retarder (B) and inhibitor (D) is therefore greater than the sum of the individual effects.

Having generally described this invention, a further understanding can be obtained by reference to certain specific examples which are provided herein for purposes of illustration only, and are not intended to be limiting unless otherwise specified.

EXAMPLES

Examples 1-10

Commercially available, stabilized styrene was freed of the tert-butyl-1,2-hydroxybenzene (TBC) stabilizer at a reduced pressure of 95 mbar and a bottom temperature of 75° C. in an inert nitrogen atmosphere. The test apparatus, which consisted of a four-neck flask equipped with a thermometer, a reflux condenser, a septum and a precision glass stirrer, was purged thoroughly with nitrogen in order to obtain an oxygen-free atmosphere. 300 g of the unstabilized styrene were added to the three-neck flask and admixed with 100 ppm of an additive according to Table 1. The additive was added either as a pure substance (examples 2-10) or as a solution (examples 10a-10c). The constant nitrogen supply through a glass frit into the styrene solution provided an inert nitrogen atmosphere over the entire test period. The styrene solution was stirred vigorously. At the start of the experiment, the flask was immersed into an oil bath preheated to 110° C. to such an extent that the stabilized styrene solution was completely immersed. After the immersion of the three-neck flask into the heated oil bath, approx. 3 g of the styrene solution were withdrawn at regular intervals via the septum, weighed accurately and added to 50 ml of methanol. The methanol mixture was stirred at room temperature for half an hour. The methanol brought about the precipitation of the polystyrene formed during the test. This was removed by filtration through a glass filter crucible. The filter residue was washed with 20 ml of methanol and then dried at 110° C. for at least 5 hours. The polystyrene remaining in the glass filter crucible was then weighed. The value determined and the initial weight were used to determine the percentage of polymer. This polymer content was plotted against the reaction time. It can be inferred from the curved profile obtained whether the additive acts as a polymerization inhibitor or as a retarder. A typical curved profile is shown in the FIGURE. The period within which a polymer content of 2% by weight had formed, and also the polymer content after 180 minutes, were determined from the curve. The results are shown in Table 1.

TABLE 1

| Example | Additive | Mode of action of the additive | Time until polymer content 2% by weight was present (in min) | Polymer content after 180 minutes (in % by weight) |
|---|---|---|---|---|
| 1 | — | — | 36 | 15 |
| 2 | 2,6-di-tert-butyl-4-(piperidinomethylene)cyclohexa-2,5-dien-1-one | — | 36 | 12.25 |
| 3 | 3,5-di-tert-butyl-4-hydroxybenzaldehyde | — | 33 | 18 |
| 4 | 2,6-di-tert-butyl-4-(cyanomethylene)cyclohexa-2,5-dien-1-one | inhibitor | 131 | 5.5 |
| 5 | 2,6-di-tert-butyl-4-(carboxymethylene)cyclohexa-2,5-dien-1-one | inhibitor | 152 | 4.5 |
| 6 | 2,6-di-tert-butyl-4-(methoxycarbonylmethylene)cyclohexa-2,5-dien-1-one | inhibitor | 139 | 5.5 |
| 7 | DNBP | retarder | 179 | 2.0 |
| 8 | 2,6-di-tert-butyl-4-benzylidenecyclohexa-2,5-dien-1-one | retarder | 165 | 2.5 |
| 9 | 2,6-di-tert-butyl-4-(ethoxymethylene)cyclohexa-2,5-dien-1-one | retarder | 116 | 3.5 |
| 10 | DTBMeOQM | retarder | 181 | 2.0 |
| 10a | DTMeOQM as 5% by weight solution in ethylbenzene | retarder | 182 | 2.0 |
| 10b | DTMeOQM as 5% by weight solution in styrene | retarder | 179 | 2.0 |
| 10c | DTMeOQM as 5% by weight solution in methanol | retarder | 180 | 2.0 |

Examples 11-18

Examples 11-18 were carried out analogously to examples 1 to 10, except that an additive mixture was added in examples 14 to 18. The results are shown in Table 2.

TABLE 2

| Example | Additive | Amount of additive (in ppm (m/m)) | Mode of action of the additive | Time until polymer content 2% by weight was present (in min) | Polymer content after 180 minutes (in % by weight) |
|---|---|---|---|---|---|
| 11 | 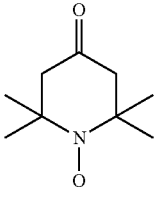 oxo-TEMPO | 100 | inhibitor | 94 | 6.5 |
| 12 | 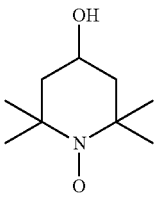 4-hydroxy-TEMPO | 100 | inhibitor | 92 | 6.5 |
| 13 | 4-hydroxy-TEMPO DNBP | 5 ppm 95 ppm | inhibitor retarder | 200 | 1.0 |
| 14 | oxo-TEMPO DNBP | 15 ppm 85 ppm | inhibitor retarder | 195 | 1.5 |
| 15 | 4-hydroxy-TEMPO DTBMeOQM | 100 ppm 10 ppm | inhibitor retarder | 218 | 0.5 |
| 16 | 4-hydroxy-TEMPO DTBMeOQM | 25 ppm 75 ppm | inhibitor retarder | 258 | 0.1 |
| 17 | oxo-TEMPO DTBMeOQM | 60 ppm 40 ppm | inhibitor retarder | 235 | 0.8 |

Examples 19-25

A saturated solution of in each case 250 mg of DTBMeOQM was made up in a solvent according to Table 3. Subsequently, the content of DTBMeOQM was determined by means of gas chromatography (GC). The solvent content was calculated in each case. These solutions were stored at room temperature for one week and then analyzed again by means of gas chromatography (GC). The results are shown in Table 3.

TABLE 3

| | | Amount of DTBMeOQM (in area %) | |
|---|---|---|---|
| Example | Solvent | Start | after 1 week |
| 19 | ethylbenzene | 100 | 100 |
| 20 | styrene | 100 | 100 |
| 21 | xylene | 100 | 99 |
| 22 | heptane | 99 | 99 |
| 23 | n-butanol | 27 | 20 |
| 24 | acetone | 100 | 82 |
| 25 | diethylene glycol monobutyl ether (DEGMBE) | 44 | 22 |

The solvents and monomers used in the examples, such as styrene, ethylbenzene, methanol, xylene, heptane, n-butanol, acetone or diethylene glycol monobutyl ether (DEGMBE), and also the additives 4-hydroxy-TEMPO, oxo-TEMPO and DNBP were purchased from Sigma Aldrich or from Merck. The additive in example 3, in contrast, was purchased from Acros. The further additives used were prepared according to the following literature references:

Synthetic Communication 2000, 30 (15), 2825 ff. (additives in examples 2, 4, 5 and 6),
Synthetic Communication 1976, 6 (4), 305 ff. (additive in example 8),
J. Org. Chem. 2002, 67, 125 ff. (additives in examples 9 and 10).

German patent application 10 2007 052891.6 filed Nov. 2, 2007, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. A monomer composition, comprising:
   an olefinically unsaturated monomer; and
   from 10 ppb (m/m) to 100 000 ppm (m/m), based on the olefinically unsaturated monomer, of at least one retarder (B) of the formula (II)

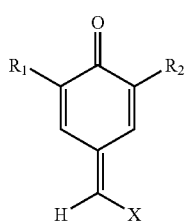

(II)

wherein
X=halogen, —O—$R_3$ or —S—$R_3$,
$R_1$, $R_2$ and $R_3$=hydrogen, alkyl having 1 to 15 carbon atoms, cycloalkyl having 3 to 15 carbon atoms or aryl group having 6 to 14 carbon atoms,
wherein the substituents $R_1$, $R_2$ and $R_3$ are the same or different and are substituted or unsubstituted.

2. The monomer composition according to claim 1, wherein, in said formula (II), the substituent X is an O—$R_3$ group.

3. The monomer composition according to claim 1, wherein, in said formula (II), $R_1$ and/or $R_2$ are independently a methyl group or tert-butyl group.

4. The monomer composition according to claim 1, wherein, in said formula (II), $R_3$ is an alkyl group having 1 to 6 carbon atoms.

5. The monomer composition according to claim 1, wherein said monomer is a vinyl-substituted aromatic, an alk-1-ene or an alka-1,3-diene, each of which is either substituted or unsubstituted.

6. The monomer composition according to claim 1, wherein said monomer is butadiene or styrene.

7. The monomer composition according to claim 1, further comprising:
   at least one solvent selected from the group consisting of saturated or unsaturated, branched and/or unbranched, ring-closed and/or open-chain aliphatic or aromatic hydrocarbons, ethers or esters, each of which has 4 to 20 carbon atoms, and methanol.

8. The monomer composition according to claim 7, which comprises,
based on the sum of the amounts of solvent and retarder,
from 45.0 to 99.9% by weight of the solvent; and
from 0.1 to 55.0% by weight of the retarder.

9. The monomer composition according to claim 7, which comprises,
based on the sum of the amounts of solvent and retarder,
from 60.0 to 98.0% by weight of the solvent; and
from 2.0 to 40.0% by weight of the retarder.

10. The monomer composition according to claim 7, wherein said solvent is benzene, toluene, ethylbenzene, xylene, styrene, methanol or mixtures thereof.

11. The monomer composition according to claim 7, which is free of nitroaromatics or nitrosoaromatics as retarders.

* * * * *